(12) United States Patent
Lee et al.

(10) Patent No.: US 8,167,836 B2
(45) Date of Patent: May 1, 2012

(54) TISSUE EXPANDER CONFIGURED FOR DRUG DELIVERY

(75) Inventors: Heejin Lee, Arlington, MA (US); Karen Daniel, Newtonville, MA (US); Grace Kim, Cambridge, MA (US); Cheryl Larrivee-Elkins, Framingham, MA (US); Michael J. Cima, Winchester, MA (US)

(73) Assignee: Taris Biomedical, Inc., Lexington, MA (US)

( * ) Notice: Subject to any disclaimer, the term of this patent is extended or adjusted under 35 U.S.C. 154(b) by 0 days.

(21) Appl. No.: 12/963,621

(22) Filed: Dec. 8, 2010

(65) Prior Publication Data

US 2011/0137244 A1    Jun. 9, 2011

Related U.S. Application Data

(60) Provisional application No. 61/267,518, filed on Dec. 8, 2009.

(51) Int. Cl.
*A61M 29/00* (2006.01)
*A61L 31/16* (2006.01)
*A61F 2/12* (2006.01)

(52) U.S. Cl. ............. 604/103.02; 604/891.1; 604/892.1; 604/93.01; 604/103; 623/7; 623/8

(58) Field of Classification Search ............... 604/890.1, 604/891.1, 892.1, 93.01, 103, 103.01, 103.02, 604/95.03, 96.01, 97.02, 915; 128/865; 623/7–8
See application file for complete search history.

(56) References Cited

U.S. PATENT DOCUMENTS

| | | | | |
|---|---|---|---|---|
| 3,852,833 | A * | 12/1974 | Koneke et al. | 623/7 |
| 4,605,412 | A * | 8/1986 | LaForest et al. | 623/8 |
| 4,826,501 | A * | 5/1989 | Grundei | 623/8 |
| 5,005,591 | A | 4/1991 | Austad | |
| 5,146,933 | A * | 9/1992 | Boyd | 128/899 |
| 5,630,843 | A | 5/1997 | Rosenberg | |
| 5,697,974 | A * | 12/1997 | Wang | 623/7 |
| 5,700,288 | A * | 12/1997 | Eaton | 623/7 |
| 5,997,574 | A * | 12/1999 | Hayes et al. | 424/422 |
| 6,283,998 | B1 * | 9/2001 | Eaton | 623/17.16 |
| 6,398,757 | B1 * | 6/2002 | Varenne et al. | 604/103.02 |
| 6,695,830 | B2 * | 2/2004 | Vigil et al. | 604/509 |
| 7,879,088 | B2 * | 2/2011 | Gao et al. | 623/4.1 |
| 2001/0004709 | A1 * | 6/2001 | Dubrul | 623/8 |
| 2001/0041936 | A1 * | 11/2001 | Corbitt, Jr. et al. | 623/8 |
| 2002/0068897 | A1 * | 6/2002 | Jenkins et al. | 604/96.01 |
| 2002/0183265 | A1 * | 12/2002 | Vogt et al. | 514/29 |
| 2003/0144734 | A1 * | 7/2003 | Dreschnack et al. | 623/8 |
| 2005/0273164 | A1 * | 12/2005 | Bowman et al. | 623/7 |
| 2007/0202151 | A1 | 8/2007 | Lee et al. | |

(Continued)

OTHER PUBLICATIONS

Berman et al., "Lidocaine Diffusion in Five Tissue Expanders: An in Vitro and in Vivo Study," Annals of Plastic Surgery, 27(4):313-317, 1991.

(Continued)

*Primary Examiner* — Quynh-Nhu H Vu
(74) *Attorney, Agent, or Firm* — Sutherland Asbill & Brennan LLP

(57) ABSTRACT

A device includes a tissue expanding portion and an enclosure positioned on a surface of the tissue expanding portion. The enclosure includes an enclosure wall and a drug formulation pocket defined by the enclosure wall. A solid drug formulation that includes a drug is housed within the drug formulation pocket.

14 Claims, 4 Drawing Sheets

U.S. PATENT DOCUMENTS

| | | |
|---|---|---|
| 2009/0149833 A1 | 6/2009 | Cima et al. |
| 2010/0003297 A1 | 1/2010 | Tobias et al. |
| 2010/0010627 A1* | 1/2010 | Matheny .................... 623/8 |
| 2010/0331770 A1 | 12/2010 | Lee et al. |
| 2011/0106248 A1* | 5/2011 | Kokott et al. ................ 623/8 |

OTHER PUBLICATIONS

Berman et al., "Lidocaine Permeability in Silicone Tissue Expanders: An in Vitro Analysis," Plastic and Reconstructive Surgery, 84(4):621-623, 1989.

Cohen et al., "Lidocaine to Relieve Pain with Tissue Expansion of the Breast," p. 489.

Derby et al., "Quantitative Analysis of Lidocaine Hydrochloride Delivery by Diffusion Across Tissue Expander Membranes," Lidocaine Diffusion and Tissue Expanders, 89(5):900-909.

FDA Breast Implant Consumer Handbook, 80 pages.

McGuire et al., "In Vivo Diffusion of Lidocaine Through Tissue Expanders," Plastic and Reconstructive Surgery, 89 (4):675-678, 1992.

Natrelle Catalog, 33 pages.

Sinow et al., "Intraluminal Lidocaine for Analgesia after Tissue Expansion: A Double-Blind Prospective Trial in Breast Reconstruction," Anals of Plastic Surgery, 28(4):320-325, 1992.

* cited by examiner

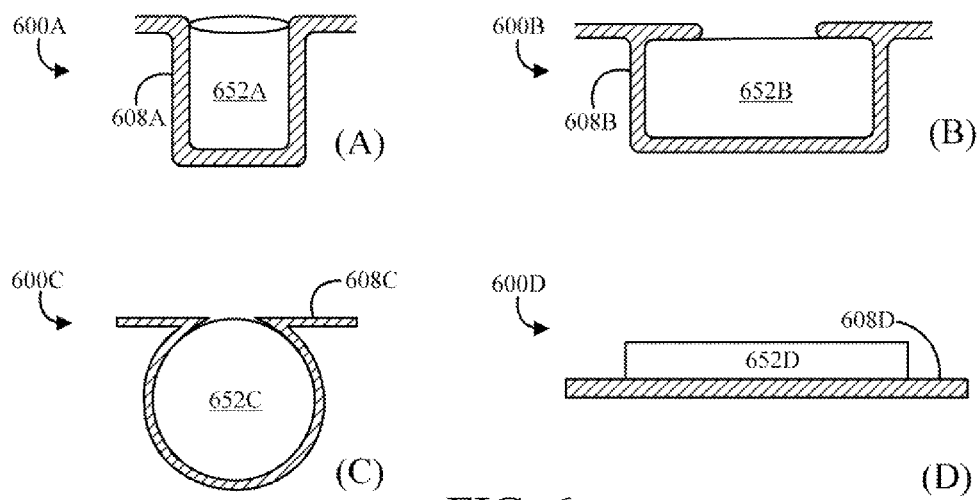
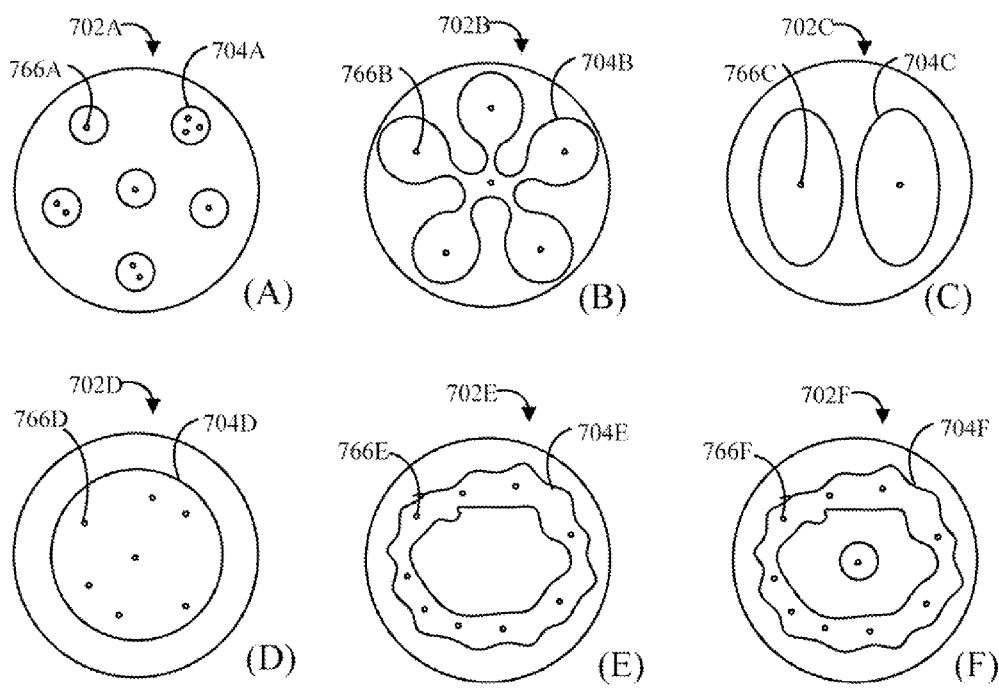
FIG. 6
FIG. 7

TISSUE EXPANDER CONFIGURED FOR DRUG DELIVERY

CROSS-REFERENCE TO RELATED APPLICATIONS

This application claims priority to U.S. Ser. No. 61/267,518, filed Dec. 8, 2009, which is incorporated by reference herein in its entirety.

BACKGROUND

The present disclosure generally relates to implantable medical devices, and more particularly to tissue expanders, which may be used in drug delivery.

A typical tissue expander includes an inflatable balloon, an injection port, and a hollow lumen that places the injection port in fluid communication with an interior of the inflatable balloon. In use, the balloon is implanted below the surface of the skin in a deflated configuration. A saline solution is then injected through the injection port to expand the balloon to an inflated configuration. The inflated balloon stretches the overlying skin, causing the skin to grow. To facilitate the slow and continued growth of healthy skin, the tissue expander is normally filled in an iterative process that includes partially inflating the balloon in an initial expansion session and further inflating the balloon in subsequent expansion sessions.

Tissue expanders are most commonly used in breast reconstruction surgery following mastectomy to form a skin pocket for holding a permanent breast implant. After the tissue expander is removed, the newly grown skin is left in place and a permanent breast implant is inserted into the empty pocket. Tissue expanders also are used to grow skin that is transplanted to other locations on the body to replace or supplement skin that has been damaged due to burn, trauma, accident, surgery, or birth defect. Increasingly, tissue expanders are used for scalp restoration, where healthy scalp tissue is grown that supports hair follicles.

One problem with tissue expansion is that the implantation site may be painful in the hours or days after the tissue expander is initially inflated. For example, many patients report feeling pain for about the first 24 to 72 hours after the expander is inflated. This pain is normally treated with pain relievers that are delivered systemically, such as a narcotic analgesic. Local drug delivery to the implantation site could be achieved directly from the tissue expander itself, although previous attempts to achieve such local delivery have proved ineffective.

Prior researchers have attempted to deliver drug directly from the inflatable balloon. The balloon was loaded with a lidocaine and saline solution with the intent of diffusing the lidocaine directly through the surface of the balloon into the surrounding environment. In vitro testing demonstrated that lidocaine did diffuse through the balloon surface. However, in vivo testing showed that the actual diffusion rate was minimal and to achieve a therapeutic delivery rate, the balloon would need to be loaded with an amount of lidocaine that would prove toxic in the event of implant rupture.

A double-chamber tissue expander also has been proposed for the purpose of achieving drug delivery. The double-chambered tissue expander includes an inner non-porous bladder, an outer porous bladder, and ports in communication with each of the bladders. In use, the outer bladder may be loaded with a lidocaine solution, while the inner bladder is loaded with an inflating solution. The expansion of the inner bladder with the inflating solution instantaneously drives the lidocaine solution from the outer bladder into the implantation site. Because the drug is delivered relatively instantaneously, however, a patient may not be adequately treated for pain experienced hours or days following inflation of the tissue expander or following subsequent inflations of the tissue expander.

It is therefore apparent that a need exists for improved systems, devices, and methods for delivering drug directly from a tissue expander. Such systems, devices, and methods desirably would provide local drug delivery from the tissue expander over an extended period.

SUMMARY

A device includes a tissue expanding portion and an enclosure positioned on a surface of the tissue expanding portion. The enclosure includes an enclosure wall and a drug formulation pocket defined by the enclosure wall. The drug formulation pocket houses a solid drug formulation that includes a drug.

The tissue expanding portion may include an expandable balloon and means for expanding the balloon from outside of the body after the balloon has been implanted in the body. The expandable balloon may define a cavity for receiving an inflating fluid. The means for expanding the balloon may include an injection port and a fill tube operable for communicating the inflating fluid from the injection port into the cavity. In some embodiments, the enclosure wall may include a portion of a wall of the expandable balloon and a cover. The cover may be attached to the portion of the wall of the expandable balloon to define the drug formulation pocket. For example, the cover may be attached to an exterior surface of the wall of the expandable balloon. The expandable balloon may be substantially impermeable to water and the drug, and the cover may be permeable to water. The cover may include an aperture for releasing the drug, the cover may be formed from a material that is permeable to the drug for releasing the drug, or some combination thereof.

In some embodiments, at least a portion of the enclosure wall may include a water-permeable material. The enclosure wall also may include an aperture that provides egress for the drug from the pocket. Also in some embodiments, at least a portion of the enclosure wall may include a material that is permeable to the drug. For example, at least a portion of the enclosure wall may include silicone.

In some embodiments, the drug formulation may substantially fill the drug formulation pocket. The drug may include at least one local anesthetic agent. For example, the drug may include lidocaine. The drug formulation may include a resorbable polymer matrix.

In another embodiment, a device includes a tissue expanding portion and a drug release portion. The drug release portion is attached to an exterior surface of the tissue expanding portion. The drug release portion includes a drug dispersed in a resorbable polymeric matrix for controlled release of the drug. The drug may include lidocaine.

In another embodiment, a method treats pain associated with tissue expansion in a patient. The method includes implanting a tissue expander device in the patient, the tissue expander device including a tissue expander portion and a drug delivery portion. The method also includes expanding the tissue expander portion. The method further includes releasing an effective amount of an analgesic or anesthetic drug from the drug delivery portion for an extended period. In some embodiments, the drug may include lidocaine. The extended period may be in the range of about 24 hours to about 72 hours. The tissue expander device may be suited for use in association with breast reconstruction.

BRIEF DESCRIPTION OF THE DRAWINGS

FIG. 6 illustrates cross-sectional side views of various embodiments of a drug delivery portions that house a drug supply in a resorbable polymer matrix.

FIG. 7 illustrates plan views of various embodiments of tissue expanders configured for local drug delivery.

DETAILED DESCRIPTION

Tissue expander devices configured for drug delivery are provided, along with methods of delivering drug from a tissue expander. In embodiments, a tissue expander is configured for the expansion of tissue and for the simultaneous release of drug to a patient in whom the tissue expander is implanted. The drug may be released locally or regionally and in an amount effective to treat, for example, pain associated with the tissue expansion process. The tissue expander may be similar in configuration to tissue expanders that are now known or are later developed, further including one or more drug delivery components or cells. The drug delivery components may be positioned about an exterior of the device to release drug into the implantation environment after the tissue expander is implanted.

In some embodiments, the tissue expander device releases a drug suited for the local treatment of pain, such as lidocaine or another local anesthetic. The local anesthetic is released from the tissue expander device in an effective amount to treat the pain associated with the expansion process. For example, the local anesthetic may be released over the hours or days following inflation of the tissue expander to treat the pain associated with the initial expansion, or the local anesthetic may be released over a more extended period, such as the period of implantation of the tissue expander, to treat the pain associated with multiple discrete expansions.

Thus, the tissue expander provides a beneficial alternative to pain management through systemic drug delivery. The tissue expander also provides a convenient alternative to other manners of local anesthetic delivery, such as injection. By delivering the anesthetic directly from the tissue expander itself, a relatively lower amount of drug may be administered to the patient and over a relatively longer period in comparison to systemic administration. Thus, the patient may receive effective pain management while avoiding the discomfort and inconvenience of repeated injections. The local treatment approach achieved by the present tissue expander can reduce or even eliminate unwanted side effects of systemic delivery while delivering therapeutically relevant concentrations locally.

I. The Tissue Expander

Figure 1:
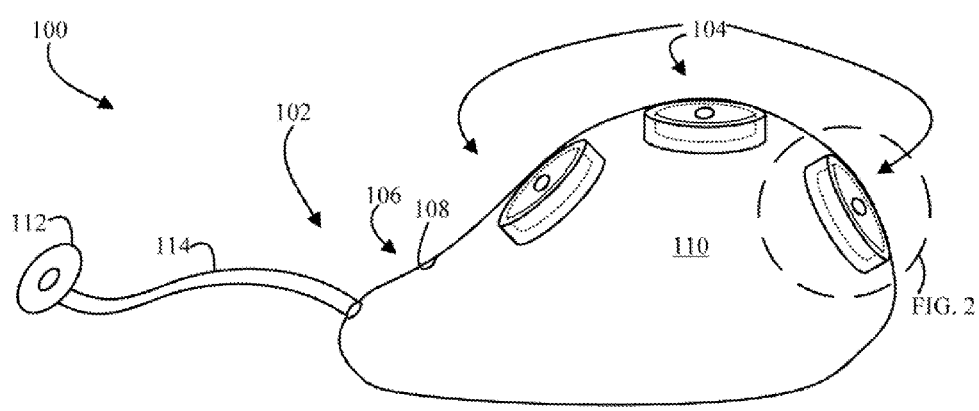
FIG. 1 is a perspective view of a tissue expander configured for local drug delivery.

The tissue expander device generally includes a tissue expansion portion and at least one drug delivery portion. The tissue expansion portion is suited for expanding tissue about the implantation environment, while the drug delivery portion is suited for delivering drug into the implantation environment. The term implantation environment generally refers to the tissue site at which the tissue expander is deployed. For example, the site may be between the pectoralis major muscle and pectoralis minor muscle. FIG. 1 is a perspective view illustrating an embodiment of a tissue expander device 100 that includes a tissue expansion portion 102 and a number of drug delivery portions 104. Each of these portions are described in further detail below.

The Tissue Expansion Portion

The tissue expansion portion generally includes an inflatable balloon and means for inflating the balloon. The inflatable balloon is suited for implantation in the body. The inflation means permits inflating the balloon from outside of the body after the balloon has been implanted.

The expandable balloon is generally reversibly transformable, or movable, between deflated and inflated configurations. Typically, the balloon is expanded with an inflating fluid, such as a saline solution or other liquid. The volume of saline solution that is placed into the balloon determines the degree to which the balloon is inflated, which in turn affects the rate of tissue expansion, the degree of tissue expansion, other characteristics of tissue expansion, or a combination thereof.

The balloon is generally defined by a balloon wall, which may be pliable and flexible so that the balloon can be inflated. The balloon wall may be elastic. The pliable or flexible nature of the balloon wall also facilitates implanting the balloon through a small incision in the body. The balloon wall also may be relatively thin to facilitate implantation. In some embodiments, at least a portion of the balloon wall may be water-permeable. Example materials that can be used to form the balloon wall include silicone, among others.

The balloon wall defines the boundary of an interior cavity. The interior cavity is configured to contain the inflating fluid. The size or volume of the interior cavity may vary depending on the degree to which the balloon is inflated.

Example means for inflating the balloon include an injection port and a fill lumen. The fill lumen places the injection port in fluid communication with the interior cavity so that an inflating fluid can be delivered from the injection port into the cavity. Once the balloon is implanted, the injection port may become positioned outside of the body, while the fill lumen may extend from the injection port, through the body, and to the balloon. Thus, an inflating fluid, such as saline solution, can be communicated from the injection port outside of the body into the balloon within the body. However, any suitable means for inflating the balloon may be employed.

One embodiment of a tissue expander portion is shown in FIG. 1. The tissue expander portion 102 is sized and shaped for expanding breast tissue for the purpose of breast reconstruction. As shown, the breast tissue expander portion 102 includes a balloon 106 formed from a balloon wall 108, an interior cavity 110 defined by the balloon wall 108, a fill lumen 114 in fluid communication with the interior cavity 110, and an injection port 112 in fluid communication with the fill lumen 114. The tissue expander portion 102 has an anatomically accurate profile or shape, although a hemispherical profile or shape may be employed in other embodiments. Most tissue expander portions for breast reconstruction have a diameter in the range of about 7.4 cm to about 17.2 cm, although other sizes can be employed.

A breast tissue expander portion is shown by way of example only, and the exact size, shape, and configuration of the tissue expansion portion can vary widely depending on the site of implantation, the route of implantation, and the reason for the tissue expansion. Alternative configurations are included in the scope of the present disclosure, which encompasses essentially any tissue expander, whether known now or developed later.

The Drug Delivery Portion

As mentioned above, the tissue expander portion is associated with at least one drug delivery portion. The drug delivery portion houses a drug supply and permits delivering drug into the body. In particular, the drug delivery portion is configured for controlled release of the drug into the body over an extended period, such as a period of hours, days, or weeks. The drug release may be driven by diffusion, osmosis, positive displacement or a combination thereof.

In some embodiments, the drug delivery portion houses the drug supply within an enclosure. The enclosure limits release of the drug into the implantation environment and at least in part controls release of the drug. In embodiments, the enclosure also includes at least one release orifice that provides egress of the drug from the enclosure. In such embodiments, the orifice at least in part controls the release of the drug. In other embodiments, the drug is released across a wall of the enclosure, in which case the wall at least in part controls release of the drug. These components are described in further detail below.

The Enclosure

In some embodiments, the drug delivery portion generally includes at least one enclosure. The enclosure houses the drug payload and modulates release of the drug into the implantation environment. In one embodiment, the enclosure is positioned adjacent to a surface of the tissue expander portion. For example, the enclosure can be attached directly to a surface of the tissue expander portion, such as on the inside or the outside of the inflatable balloon.

In particular, the enclosure includes an enclosure wall that defines a pocket or cell for receiving the drug supply. The enclosure wall holds the drug supply, i.e., the drug payload. In some embodiments, the enclosure wall substantially or completely surrounds or encases the drug supply. Thus, the enclosure wall may serve as a protective sheath about the drug supply, thereby limiting and controlling release of the drug from the pocket. In other embodiments, the enclosure wall may not substantially or completely surround the drug supply. In such embodiments, the drug may be formulated with a matrix material for modulating drug release kinetics. For example, the matrix material may include a polymer, such as a resorbable polymer, such as PLA, PGA, PLGA, or the like. In such embodiments, the drug/matrix material composite may be configured to slow or control release of the drug into the implantation environment. The matrix material may work in concert with or independently of the enclosure wall to control the drug release kinetics.

In most embodiments, the enclosure wall includes a discrete portion of the balloon wall and a separate cover that is attached to the discrete portion of the balloon wall. The cover can be attached on either the inside or the outside of the balloon, although the outside may be preferred for ease of manufacturing. In such embodiments, the pocket or reservoir for housing the drug supply is formed between the cover and the balloon wall. In other embodiments, the enclosure wall may not include any portion of the balloon wall. In such embodiments, the enclosure wall may be formed from a completely separate wall that is enclosed to define the pocket or reservoir and is independently attached to the tissue expansion portion. In still other embodiments, the enclosure wall may include only a portion of the balloon wall, which may be extend about the drug supply to hold the drug supply against the tissue expander portion.

In some embodiments, the enclosure includes at least one orifice that provides egress for the drug from the pocket. The drug may be driven through the orifice via osmotic pressure or diffusion. In embodiments in which the cover is attached to the outside of the balloon, the orifice may be formed through the cover. In embodiments in which the cover is attached to the inside of the balloon, the orifice may be formed through the balloon wall adjacent to the pocket. In some embodiments, a number of orifices may be formed through the enclosure to increase the rate of release of the drug from the pocket, as described in further detail below. However, the orifice may be omitted completely, such as in cases in which the drug can diffuse directly through the cover, balloon wall, or other portion of the enclosure.

In some embodiments, at least a portion of the enclosure is permeable to the drug and provides egress for the drug via diffusion. In embodiments in which the cover is attached to the outside of the balloon, the cover may be permeable to the drug. In embodiments in which the cover is attached to the inside of the balloon, the balloon wall may be permeable to the drug, at least about the pocket. Any suitable portion of the cover or balloon wall may be permeable to the drug for releasing the drug via diffusion, such as in cases in which the enclosure does not include an aperture for releasing the drug.

In some embodiments, the enclosure includes a dimple or depression. The dimple may form at least a portion of the pocket for receiving the drug supply. The dimple or depression may be formed in the cover, the balloon wall, or both. The dimple may facilitate holding the drug supply, particularly in embodiments in which the drug supply is provided in a solid form. The size and shape of the dimple is selected based on the size and shape of the drug supply to be inserted therein, or vice versa.

In some embodiments, the dimple is substantially cylindrical in shape. A diameter of the dimple may be larger than a height of the dimple to accommodate a similarly shaped drug tablet, for reasons described below. However, the dimple or depression may be omitted completely, in which case the enclosure may be formed by stretching one or both of the cover and balloon wall about a solid drug formulation, or by providing slack between the cover and balloon wall for holding a drug in semi-solid or liquid formulation.

In some embodiments, the enclosure may be shaped so that a portion of its surface area is exposed to the implantation environment, such as by being in direct contact with the implantation environment, by being positioned directly adjacent to the implantation environment, or some combination thereof. The exposed surface area of the enclosure may receive fluid (e.g., water, interstitial fluid) directly from implantation environment, such as to solubilize a solid drug supply in the enclosure, to create an osmotic pressure in the enclosure for driving solubilized drug from an orifice, or a combination thereof. The exposed surface area also may release drug directly to the implantation environment, such as through an orifice or through the exposed surface area itself. The exposed surface area may be any portion of the balloon wall, the cover, or a combination thereof.

In some embodiments, a significant portion of the surface area of the enclosure may be exposed to the implantation environment. For example, the entire cover may be exposed to the implantation environment in embodiments in which the cover is attached to the exterior of the balloon. Exposing a significant portion of the enclosure surface area to the implantation environment facilitates directing more water into the enclosure, such as to solubilize the drug supply more rapidly or to increase the osmotic pressure developed within the enclosure. For example, a solid drug formulation positioned adjacent to the exposed surface area is positioned for ready solubilization. By increasing the exposed surface area, more of the solid drug formulation may be positioned for ready solubilization, increasing the release rate.

Exposing a significant portion of the enclosure surface area to the implantation environment also facilitates delivering drug. For example, orifices formed through the exposed surface area may be in direct fluid communication with the implantation environment for releasing the drug. By increasing the exposed surface area, more orifices can be placed in direct fluid communication with the implantation environment to release more drug, to treat a relatively larger area, or some combination thereof. Also, any portion of the exposed surface area that permeable to the drug may be in direct fluid communication with the implantation environment for releasing the drug. By increasing the exposed surface area, more of the enclosure can be placed in direct fluid communication with the implantation environment for releasing the drug.

An example shape for the enclosure that results in a relatively large portion of the enclosure surface area being exposed to the implantation environment is a cylindrical shape, wherein the diameter of the enclosure extending along the surface of the device exceeds a height or depth of the enclosure into the device.

Figure 2:
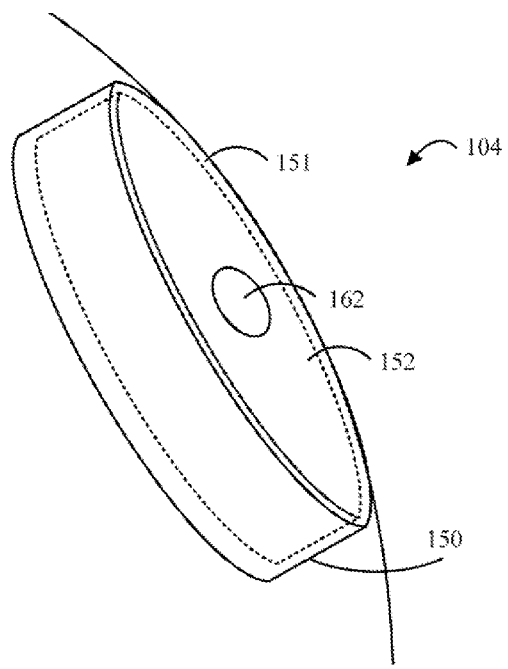
FIG. 2 is a close-up, perspective view of a drug delivery portion of the tissue expander shown in FIG. 1.

An example is shown in FIG. 2, which illustrates a substantially cylindrical enclosure 150 formed in a drug delivery portion 104. The enclosure 150 includes a large circular end face 151 that is exposed to the implantation environment. The end face 151 has a relatively large surface area in comparison to a side wall of the enclosure 150, as shown in the illustrated embodiment. Thus, a solid drug formulation 152 adjacent to the end face 151 is positioned for ready solubilization and for drug release, either through an orifice formed through the end face 151 or by diffusion of directly through the end face itself. However, other shapes and configurations are possible. In other embodiments, the enclosure may not have a substantial portion or any portion of the enclosure wall exposed to the implantation environment.

In some embodiments, the pocket in the enclosure is substantially filled by the drug to maximize the amount of drug that can be delivered. Filling the pocket may also reduce the induction time of initial release of drug from the pocket, as further described below.

Figure 3:
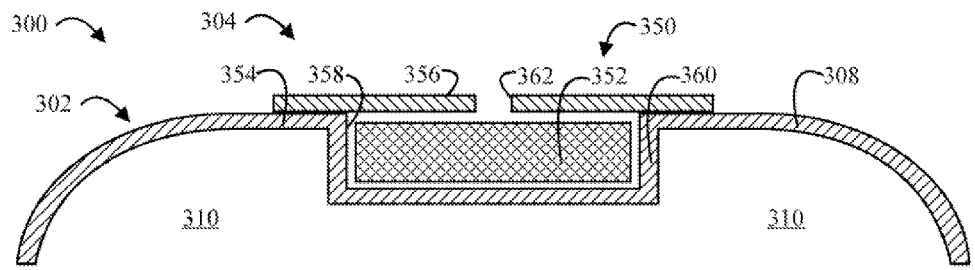
FIG. 3 is a cross-sectional, partial view of an embodiment of a tissue expander configured for local drug delivery.

An example configuration is shown in FIG. 3, which is a cross-sectional, partial view of an embodiment of a tissue expander device 300, illustrating a drug delivery portion 304 formed on a surface of a tissue expander portion 302, particularly on an exterior surface of the balloon wall 308 adjacent to the interior cavity 310. The drug delivery portion 304 includes an enclosure 350 and a drug formulation 352. The enclosure 350 is formed from a balloon wall portion 354 and a cover portion 356. The enclosure 350 defines a pocket 358, and the drug formulation 352 is positioned in the pocket 358. Once the drug formulation 352 is so positioned, the enclosure 350 substantially surrounds the drug formulation 352.

In the illustrated embodiment, the cover 356 is attached to an exterior surface of the balloon wall portion 354. A dimple or depression 360 is formed in the balloon wall portion 354 for receiving the drug formulation 352. The drug formulation 352 is positioned in the dimple 360 and the cover 356 is positioned adjacent to the balloon wall portion 354 in register with the dimple 360. The cover 356 is attached to the balloon wall portion 354 with an adhesive, such as a silicone adhesive or other medical grade adhesive. Other attachment means may also be used. An orifice 362 is formed through the cover to provide egress of the drug formulation 352 from the pocket 358, although the orifice is not necessary and can be omitted, such as in embodiments in which at least a portion of the cover 356 is permeable to the solubilized drug for releasing the drug via diffusion.

Figure 4:
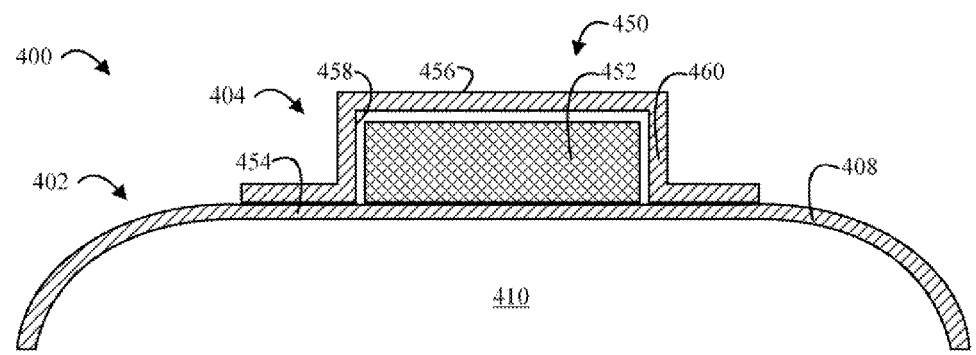
FIG. 4 is a cross-sectional, partial view of another embodiment of a tissue expander configured for local drug delivery.

FIG. 4 is a cross-sectional, partial view of another embodiment of a tissue expander device 400, illustrating a drug delivery portion 404 formed on a surface of a tissue expander portion 402, particularly on an exterior surface of the balloon wall 408 opposite from the cavity 410. The embodiment of FIG. 4 is similar to the embodiment of FIG. 3, except that the dimple or depression 460 is formed in the cover 456 instead of the balloon wall portion 454 and the orifice is omitted. In such an embodiment, the cover 456 may be permeable to the drug. An orifice also may be provided, in which case the orifice would be formed in the cover 456.

Figure 5:
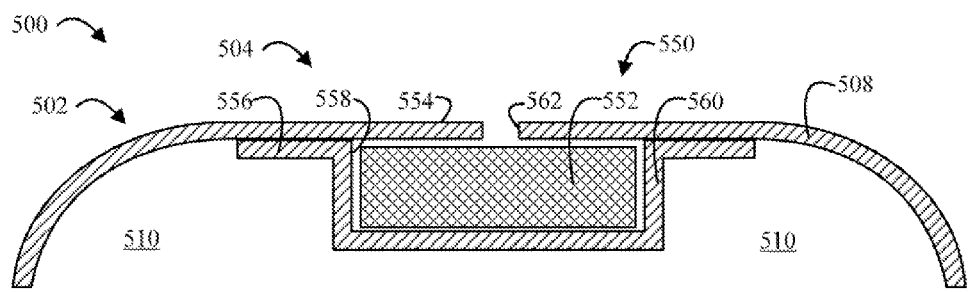
FIG. 5 is a cross-sectional, partial view of another embodiment of a tissue expander configured for local drug delivery.

FIG. 5 is a cross-sectional, partial view of another embodiment of a tissue expander device 500, illustrating a drug delivery portion 504 formed on a surface of a tissue expander portion 502, particularly on an interior surface of the balloon wall 508 within the cavity 510. The embodiment of FIG. 5 is similar to the embodiment of FIG. 4, except that the cover 556 is positioned within the cavity 510 and is attached to the balloon wall 508 on its interior surface. In such an embodiment, the orifice is formed through the balloon wall portion 554 instead of through the cover 556. However, the orifice may be omitted, in which case the balloon wall portion 554 may be permeable to the drug for releasing the drug from the pocket. In the illustrated example, the dimple 560 is formed in the cover 556, but it should be understood that the dimple 560 alternatively may be formed in the balloon wall 508, such in embodiments in which the cover 556 is attached to the interior surface of the balloon wall 508. It also should be understood that the dimple or depression may be formed in a portion of both the balloon wall and the cover. The dimple or depression also may be omitted completely, in which case the cover and the balloon wall can be stretched about a solid drug formulation, or slack can be provided between the cover and balloon wall for loading a semi-solid or liquid drug formulation.

In certain embodiments, the enclosure is configured to imbibe or receive water or other fluid from one or both of the implantation environment and the cavity of the tissue expander portion. In embodiments in which the drug is in solid or semi-solid formulation, the fluid may solubilize or dissolve the drug. The fluid also may generate an osmotic pressure within the enclosure to drive the solubilized drug from the orifice.

So that fluid can enter the pocket, at least a portion of the enclosure wall may be permeable to water, including any portion of the cover, any portion of the balloon wall about the enclosure, or a combination thereof. Fluid also may enter the pocket through the orifice. The exact configuration of the enclosure wall determines whether fluid enters the pocket from the implantation environment, from the cavity of the tissue expander portion, both, or neither.

In most embodiments, the cover is formed from a water-permeable material, and the balloon is formed from a material that is substantially impermeable to water. The cover is attached to the exterior surface of the balloon so that fluid enters the pocket primarily by passing through the cover from the implantation environment. However, other configurations are possible.

In one embodiment, the balloon wall is formed of a material that is permeable to water so that fluid can enter the pocket through the balloon wall. In such embodiments, the cover may or may not be water-permeable. The balloon wall may receive fluid from the implantation environment or the interior cavity depending on how the enclosure is configured. For example, fluid may pass through the balloon wall from the implantation environment if the cover is attached inside of the balloon, as shown in FIG. 5.

In another embodiment, both the cover and the balloon wall are water-permeable so that fluid can enter the pocket from both the implantation environment and the cavity. The balloon wall also may be water-permeable about the enclosure and impermeable in other areas.

The balloon wall and cover may have different permeabilities from each other. For example, the cover may be more water-permeable than the balloon wall so that the majority of the fluid enters the pocket through the cover. Examples of suitable water-permeable materials that can be used to form the cover or any portion of the balloon include silicone, among others. The water-permeability of a silicone wall may vary depending on the thickness of the wall, with a thin wall being relatively more water permeable than a thick wall. Other biocompatible materials also may be used. The material forming the enclosure can be porous or non-porous. For example, with a drug having a low aqueous solubility, a porous silicone may be useful. In still other embodiments, both the cover and the balloon wall are substantially impermeable to water, in which case the drug may be in liquid, gel, or slurry formulation, among others, for release from the orifice or via diffusion across the enclosure wall.

In some embodiments, the enclosure is configured to release drug via diffusion through the cover, the balloon wall, or some combination thereof. So that the drug can be released from the pocket, at least a portion of the enclosure wall may be permeable to the drug. In such embodiments, the cover may be formed from a material that is permeable to the drug, and the balloon may be formed from a material that is substantially impermeable to drug. The cover may be attached to the exterior surface of the balloon so that drug exits the pocket primarily by passing through the cover into the implantation environment. However, other configurations are possible. For example, a portion of the balloon wall may be permeable to the drug, such as in embodiments in which the cover is attached to the interior of the balloon. The enclosure also may not be permeable to the drug in embodiments that include an aperture for drug release.

The cover can be made of biodegradable/bioabsorbable rubber materials, such as poly(glycerol) sebacate (PGS) films. In such cases, the drug delivery portion may eventually degrade or resorb so that only the tissue expanding portion remains. The cover may be configured to remain intact throughout the course of drug delivery and to degrade or resorb following completion of drug delivery.

In some embodiments, the enclosure wall is thinner than the balloon wall, in whole or in part. More particularly, all or part of the enclosure wall may be thinner than all or part of the balloon wall. The thinner nature of the enclosure wall facilitates directing water into the enclosure to solubilize the drug and/or to create an osmotic pressure for driving the solubilized drug from the orifice. The thicker nature of the balloon wall facilitates maintaining structural integrity of the tissue expander, reducing the likelihood of rupture. The thicker nature of the balloon wall also may reduce the permeability of the wall to water or the drug. In embodiments in which the enclosure is formed by attaching a cover to a portion of the balloon wall, the cover may be relatively thinner than the portion of the balloon wall. The thinner cover serves as the primary surface for water ingress into the pocket and as the primary surface for drug egress, either through an orifice in the cover or across the cover itself. Such a configuration facilitates manufacturing, as the balloon can be manufactured with a relatively uniform thickness and the thinner cover can be attached subsequently.

In some embodiments, the cover is a silicone membrane having a thickness in the range of about 50 micron to about 200 micron, depending on the desired rate of drug release, and the balloon has a thickness in the range of about 0.38 mm to about 1 mm. However, other configurations are possible.

The enclosure is configured to release the drug through any portion of the enclosure wall, through the orifice, or a combination thereof. For example, the drug may be released from the enclosure via diffusion across the enclosure wall, via diffusion from the orifice, via passage through the orifice due to osmotic pressure within the enclosure, or a combination thereof. Release of the drug also may be driven by a positive displacement, such as due to a deformation or elastic contraction of the enclosure walls.

As further described below, the release rate of the drug from the drug delivery portion generally is controlled by the design of the combination of device components, including but not limited to the configuration of the enclosure wall, the configuration of any orifice or orifices, the solubility and other properties of the drug, and the formulation of the drug. It should be noted that the term configuration includes parameters such as size and shape, along with materials of construction and composition, among others.

In some embodiments, the release rate of the drug from the drug delivery portion is controlled at least in part by the design of the drug formulation, which may include a resorbable matrix material. The drug formulation can be integrated directly into the surface of the tissue expander portion, such as by forming a dimple or depression in the balloon wall or by stretching the balloon wall about the drug formulation. The drug formulation also can be attached directly to the surface of the balloon wall using an adhesive. In such embodiments, the cover may or may not be provided.

Examples are shown in FIG. 6. For example FIG. 6A illustrates a device 600A that includes a solid drug formulation 652A surrounded by a portion of the balloon wall 608A. The balloon wall 608A forms the enclosure. In particular, the balloon wall 608A forms a cylindrical pocket that is shaped to receive a cylindrically shaped drug formulation 652A. The drug formulation 652A is retained in the pocket by the balloon wall 608A, which exerts a slight force on the drug formulation. The balloon wall 608A does not extend all the way about the drug formulation 652A, but instead remains partially open, forming an orifice for releasing the drug 652A into the implantation environment, following dissolution of the drug. Other configurations are also possible. For example, in FIG. 6B, the balloon wall 608B forms a slight retention flange for retaining the drug formulation 652B in the pocket. The drug formulation also may have other shapes. For example, in FIG. 6C, the drug formulation is spherical in shape, and the balloon wall forms a spherical pocket. The spherical drug formulation 652C is retained in the pocket by a retaining flange on the balloon wall 608C. The drug formulation also may be slightly larger than the pocket and may protrude from the pocket. For example, in FIG. 6C, the spherical drug formulation 652C may have a larger diameter than the pocket and may be retained in the pocket due to its increased diameter, in which case the drug formulation can protrude slightly into the implantation environment. In these and in other embodiments, the cover may be omitted, as the composition of the drug formulation 652 may control the release rate into the implantation environment. For example, FIG. 6D illustrates a solid drug formulation 652D attached directly to the balloon wall 608D. Alternatively, a cover may be provided to further modulate release.

Apertures

As mentioned above, the enclosure may include one or more apertures or orifices in some embodiments. The apertures or orifices permit release of the drug from the pocket. The apertures or orifices pass through a portion of the enclosure wall, such as through the cover or the balloon wall, to provide a passageway for drug release from the drug delivery portion. Generally, the apertures are formed through a portion of the enclosure wall that is exposed to the implantation environment so that the apertures place the drug formulation in direct fluid communication with the implantation environment. Embodiments of orifices 162, 362, 562 are shown in FIGS. 1, 3 and 5.

The location of the apertures can be selected to target drug delivery into selected locations in the implantation environment. For example, the apertures may be spaced about the tissue expander device to release drug into any selected portion of the implantation environment. The apertures also may be spaced about the tissue expander device to release drug into substantially the entire implantation environment. Such a configuration may be especially useful in embodiments in which the drug is released to treat pain associated with the tissue expansion process.

The number and size of the orifices can be configured to achieve a desired release rate of the drug from the device. The effect of orifice number on release rate is described in further detail below with reference to Example 1.

In embodiments in which the device is intended to operate primarily as an osmotic pump, the size of each aperture may be selected such that the aperture is small enough to minimize or otherwise reduce diffusion of the drug through the aperture, and yet large enough to prevent clogging with particulate matter or excessive buildup of hydrostatic pressure in the pocket, which otherwise could increase the volume of fluid in the pocket or reservoir, causing the drug delivery portion to swell. An excessive increase in hydrostatic pressure within the pocket may be prevented by ensuring the size of the aperture is large enough and/or by spacing a number of apertures about the enclosure. Within these constraints on aperture size and number, the size and number of apertures may be varied to achieve a selected release rate of drug. In exemplary embodiments, the diameter of any one aperture is between about 20 µm and about 300 µm (e.g., 20 to 100 µm, 25 to 75 µm, etc.). In one example, each aperture is circular and has a diameter between about 25 µm and about 500 µm. In another example, each aperture is circular and has a diameter between about 20 µm and about 75 µm. In one particular example, each aperture has a diameter of about 50 µm. In embodiments in which the device operates primarily by diffusion through the aperture, the apertures may be in this range or larger. A single device may have apertures of two or more different sizes.

The aperture typically is circular in shape, although other shapes are possible and envisioned, typically depending on manufacturing considerations. Examples of processes for forming the apertures include mechanical punching, laser drilling, or molding. In cases in which the balloon wall is stretched about the drug formulation, the aperture may be an opening or exposed area where the balloon wall does not cover the drug formulation. In one embodiment, the apertures are drilled by laser ablation through the wall of the enclosure, such as the silicone cover. For example, the aperture may be generated using an ultraviolet excimer laser micromachining system. In such embodiments, the aperture may be slightly tapered from an exterior to an interior of the wall. For example, the aperture may have a diameter of about 55 µm along the outer surface of the wall, and the aperture may have a diameter of about 45 µm along the inner surface of the wall, although any other configuration is possible. A person of skill may be able to use laser ablation to drill in a medical grade polymer, via either through-hole drilling or depth-controlled drilling, to create a well-defined hole with a diameter as small as 0.05 µm. The apertures may be created before or after the drug is loaded into the pocket.

In another embodiment, one or more apertures are formed in an orifice structure positioned in the enclosure wall. The orifice structure includes an orifice. The orifice structure may be a precision orifice known in the art (available for example from Bird Precision Orifices, Swiss Jewel Company). The orifice structure can be inserted within and/or attached to the enclosure wall with silicone adhesives. In one example, the orifice structure may be a precision orifice structure made of ruby or sapphire having an outer diameter of about 1.5 mm or smaller.

In some embodiments, a drug delivery portion includes an array of two or more discrete apertures in spaced positions. The two or more apertures may be in fluid communication with a single reservoir in the pocket or with a plurality of separate reservoirs formed in the pocket by one or more dividing walls.

In some embodiments, a degradable membrane is disposed over or in the orifice, such as in register with the orifice, to control the initial release of the drug formulation through the orifice. In one embodiment, the degradable membrane is in the form of a uniform coating covering the outer surface of, for example, the enclosure or the inflatable balloon. In another embodiment, a discrete degradable membrane is provided substantially within the orifice to block the orifice. Combinations of two or more degradable membranes may be used to delay or control release from one orifice. The membranes may be formed, for example, of a resorbable synthetic polymer (such as polyester, a poly(anhydride), or a polycaprolactone) or a resorbable biological material (such as cholesterol, other lipids and fats). Additional details about the degradable membranes are described in U.S. Patent Application Publication No. 2009/0149833.

The Drug and Drug Formulation

The drug can include essentially any therapeutic, prophylactic, or diagnostic agent that would be useful to deliver locally or regionally from a tissue expander. The drug formulation may consist only of the drug or may include one or more pharmaceutically acceptable excipients. The drug may be a biologic. The drug may be a metabolite. As used herein, the term "drug" with reference to any specific drug described herein includes its alternative forms, such as salt forms, free acid forms, free base forms, and hydrates. Combinations of drugs may also be used. Combinations of two or more drugs, stored in (and released from) the same or separate compartments in the device are envisioned.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation includes a reduced amount of excipients or no excipients, to reduce the size of the device or to increase the amount of drug that can be delivered from a device of a given size.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. Thus, the drug may be formulated to have a high or low solubility depending on the intended release mode. The release of lidocaine hydrochloride monohydrate and lidocaine base through a silicone wall with one aperture, a number of apertures, or no apertures is described in Example 1 of U.S. patent application Ser. No. 12/825,215, which is incorporated by reference herein in its entirety. In one embodiment, the drug is formulated to improve its apparent solubility in the implantation environment. For example, lidocaine hydrochloride may be suited for release through an orifice driven by osmotic pressure, while lidocaine base may diffuse directly through a thin silicone membrane.

In one embodiment, the drug is selected to provide pain relief to the patient. A variety of anesthetic agents, analgesic agents, and combinations thereof may be used for this purpose. Representative examples of suitable such agents include lidocaine hydrochloride, procaine hydrochloride, salicyl alcohol, tetracaine hydrochloride, phenazopyridine hydrochloride, acetaminophen, acetylsalicylic acid, flufenisal, ibuprofen, indoprofen, indomethacin, naproxen, codeine, oxycodone, and fentanyl citrate. In one embodiment, the device is used to deliver one or more local anesthetic agents. The local anesthetic agent may be a cocaine analogue. In particular embodiments, the local anesthetic agent is an aminoamide, an aminoester, or a mixture thereof. Combinations of different aminoamides or combinations of different aminoesters are envisioned. Representative examples of possible aminoamides include lidocaine, prilocaine, mepivacaine, bupivacaine, articaine and ropivacaine. Representative examples of possible aminoesters include benzocaine, procaine, proparacaine, and tetracaine. These local anesthetics may be weak bases that are formulated as a salt, such as the hydrochloride salt, to render them water-soluble.

In one particular embodiment, the drug formulation includes one or more of hyaluronidase, lidocaine, epidermal growth factor, and an osmotic agent.

In certain embodiments, the drug is used to treat inflammatory conditions. Non-limiting examples of specific drugs for inflammatory conditions include lidocaine, glycosaminoglycans (e.g., chondroitin sulfate, sulodexide), pentosan polysulfate sodium (PPS), dimethyl sulfoxide (DMSO), mitomycin C, heparin, flavoxate, or a combination thereof.

In another embodiment, the drug is one useful in the treatment of cancer. For example, drugs that may be used include antiproliferative agents, cytotoxic agents, chemotherapeutic agents, or a combination thereof. The drug may be a biologic, and it may comprise a monoclonal antibody, a TNF inhibitor, an anti-leukin, or the like. The drug treatment may be coupled with a conventional radiation or surgical therapy targeted to the cancerous tissue.

In still another embodiment, the drug is one useful in the treatment of infections. For example, the drug may be selected from antibiotics, antibacterial, antifungal, antiprotozoal, antiviral and other antiinfective agents. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In various embodiments, the tissue expander is used to deliver one or more drugs, such as analgesics or anaesthetics (e.g., lidocaine, bupivacaine, mepivacaine, prilocaine, articaine, and ropivacaine); anticholinergics; antimuscarinics such as oxybutynin or propiverine; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists.

Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug. In one particular embodiment, an osmotic agent is included to control the water permeation rate into the pocket, thereby controlling the release rate of the drug formulation into the body.

The excipient may be a matrix material, selected to modulate or control the rate of release of the drug from the pocket. In one embodiment, the matrix material may be a resorbable or non-resorbable polymer. Examples of a resorbable polymer matrix drug formulations are shown in FIG. 6. Because the matrix material modulates release of the drug, the cover may be omitted and the drug formulation may be exposed directly to the implantation environment, as shown. In another embodiment, the excipient comprises a hydrophobic or amphiphilic compound, such as a lipid (e.g., selected from fatty acids and derivatives, mono-, di- and triglycerides, phospholipids, sphingolipids, cholesterol and steroid derivatives, oils, vitamins and terpenes).

The drug may be formulated to provide a temporally modulated release profile or a more continuous or consistent release profile. Pulsatile release can also be achieved from a plurality of drug delivery portions, such as through the use of different degradable membranes that temporally stagger the release from each of several drug delivery portions.

In a preferred embodiment, the drug formulation is in a solid form. In particular, the drug formulation may be a solid, monolithic structure that substantially retains a selectively imparted shape at the temperature and pressure conditions to which the delivery device normally will be exposed during assembly, storage, and handling before implantation. Providing a solid drug formulation advantageously increases the amount of drug that can be released from an enclosure of a selected volume and/or permits delivering the same amount of drug from an enclosure of a reduced size. The solid drug formulation may be in the form of a compressed tablet, pellet, bead, or rod, although other configurations are possible. In one embodiment, the drug formulation is a tablet made by a direct compression tableting process or other tableting process. Such tableting processes are known in the pharmaceutical arts. In another embodiment, the drug formulation is a tablet made by a molding process. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics. The drug formulation also may be in powdered form.

The solid drug formulation may be sized and shaped to substantially fill the pocket. Filling the pocket increases the amount of drug formulation that can be released from an enclosure of a selected size. Filling the pocket also reduces the amount of air in the pocket, which decreases the lag time before initial release of the drug formulation. In some embodiments, the pocket is sized slightly smaller than the drug formulation, so that the enclosure snugly retains the drug formulation in the pocket. The enclosure may be formed from an elastomeric material such as silicone for this purpose. The elastomeric enclosure wall may slightly stretch about the drug formulation when loaded in the pocket, snugly encasing the drug formulation therein. In some embodiments, a number of drug tablets may be used. The drug tablets may have any shape, and the number and shape of the drug tablets may be selected so that the when the drug tablets are loaded in the enclosure, the enclosure is substantially filled.

An embodiment of a solid drug formulation is shown in FIG. 2. The drug formulation 152 is a solid drug tablet that is sized and shaped to substantially fill the cylindrically shaped enclosure 150 and/or dimple. Thus, the drug tablet 152 is substantially cylindrical in shape. The tablet 152 has a width in a direction extending along a surface of the device that exceeds a height or depth in direction extending into the device. Thus, a large portion of the surface area of the drug tablet 152 is positioned directly adjacent to an implantation environment, separated only by the enclosure wall. Such a configuration facilitates solubilizing the drug formulation 152 with water directed into the enclosure 150 from the implantation environment and releasing the drug formulation 152 through an orifice 162 that is in direct fluid communication with the implantation environment. The drug formulation 152 is sized to substantially fill the enclosure 150 to limit the induction time of initial release, although the drug formulation 152 is illustrated as being slightly smaller than the enclosure merely to facilitate visual differentiation of the enclosure 150 and the drug formulation 152.

In the illustrated embodiment, the drug delivery portion 104 is suited for treating pain associated with the expansion of breast tissue. The drug units 152 may be cylindrical tablets having a diameter of about 0.8 cm and a length of about 0.2 cm. Each tablet 152 includes about 100 mg of lidocaine hydrochloride. Each tablet 152 weighs about 100 mg, assuming a packing density of about 1 g/mL. However, other sizes, shapes, drug contents, amounts, and packing densities can be used. For example, a spherical embodiment of a solid drug formulation is shown in FIG. 6.

Other Device Features

In one embodiment, the device includes at least one radio-opaque portion or structure to facilitate detection or viewing of the device by a medical practitioner as part of the implantation or retrieval procedure. In one embodiment, the device is constructed of a material that includes a radio-opaque filler material, such as barium sulfate or another radio-opaque material known in the art. A silicone wall may be made radio-opaque (for X-ray imaging or fluoroscopy) by blending radio-opaque fillers, such as barium sulfate or another suitable material, during the processing of the wall. Ultrasound imaging can also detect silicone in vivo, but it may suffer from lack of resolution to be able to correctly image the device. Fluoroscopy may be the preferred method during deployment/retrieval of the device by providing accurate real-time imaging of the position and orientation of the device to the practitioner performing the procedure.

In one embodiment, the device further includes at least one retrieval feature. The retrieval feature may be a structure that facilitates removal of the device from the body cavity. In some embodiments, the filling lumen may serve as the retrieval feature.

The drug reservoir portion can be partially or wholly coated with a coating or a sheath, which may augment control of drug release kinetics, as described in U.S. Application Publication No. 2009/0149833 A1.

Combination of Components

The tissue expander device disclosed above is configured to release a therapeutically effective amount of the drug into the implantation environment over an extended period. The extended period encompasses the initial expansion of the tissue expander and may encompass one or more of the subsequent expansions of the tissue expander. For example, the extended period may be in the range of about 24 to 72 hours, or longer. The drug may be released in a controlled manner that is substantially continuous, such as over a majority of the extended period.

In some embodiments, the drug delivery portion operates essentially by diffusion. The drug formulation is diffused from the enclosure through the one or more orifices, all or some of the enclosure wall, or a combination thereof. In other embodiments, the drug delivery portion operates as an osmotic pump. At least a portion of the enclosure is formed from a water-permeable material, such as a silicone, so that water or bodily fluid can permeate through the enclosure following implantation of the device. The water or fluid creates an osmotic pressure in the enclosure that drives the drug from the orifices at a controlled rate. In embodiments in which the drug is in solid form, the water or fluid is also imbibed by the drug, solubilizing the drug so that the solubilized drug can be released from the device. In still other embodiments, the device may operate by a combination of osmosis and diffusion.

The release rate of the drug from the drug delivery portion generally is controlled by the design of the combination of device components, including but not limited to the configuration of the enclosure wall, the configuration of the one or more orifices, and the solubility and other properties of the drug, and the drug formulation. In particular, the delivery rate is affected by the surface area of the enclosure; the thickness of the enclosure; the type of material used to form the enclosure and its permeability; the shape, size, number and placement of the orifices, if any; and the drug formulation mass and dissolution profile, among other factors. The delivery rate can be predicted from the physicochemical parameters defining the particular drug delivery system, according to well known principles, which are described for example in Theeuwes, *J. Pharm. Sci.*, 64(12):1987-91 (1975) and in U.S. Patent Application Publications No. 2009/0149833. The number of orifices may be increased to increase the release rate from the device, as described below in Example 1.

The release rate of the drug from the drug delivery portion may also be controlled by the composition of the drug formulation. For example, the drug formulation may be in the form of a drug combined with a matrix material that releases drug at a controlled rate due to degradation of and/or diffusion through the matrix material.

In some embodiments, a number of discrete drug delivery portions are spaced about the device, each of the drug delivery portions playing a role in the overall release of drug into the implantation environment. Including multiple discrete drug reservoir portions may facilitate delivering drugs into different locations in the implantation environment, delivering multiple different drugs into the implantation environment, delivering different forms of drugs (such as liquid and solid) into the implantation environment, delivering drugs at varying rates into the implantation environment, or a combination thereof.

An example of such an embodiment is shown in FIG. 1, which illustrates three drug delivery portions 104 positioned about the surface of the tissue expander portion 102. Each drug delivery portion houses a portion of the drug payload, and together the drug delivery portions house the entire drug payload. Any number or positioning of drug delivery portions may be used to achieve the desired release characteristics. Positioning disparate drug delivery portions in different locations on the implant facilitates targeting drug delivery to a larger area. For example, the illustrated device 100 is configured to release drug in multiple directions along the front side of the device. In embodiments, the drug delivery portions may also be positioned about the back side of the device to release drug in an opposing direction. Thus, the device can deliver drug toward any portion of the implantation environment. In some embodiments, the device is lined by drug delivery portions so that substantially the entire implantation environment is treated. Such a configuration may be desirable in cases in which the device delivers a drug suited for treating pain associated with the tissue expansion process, so that a local anesthetic or analgesic can be delivered about substantially the entire tissue area that is in contact with the expander.

The different drug delivery portions may house the same or different drugs or drug formulations, for example to deliver different therapeutic agents and/or the same therapeutic agent at different rates/times. Thus, one device may be used to release a number of different drugs or to release any given drug according to a number of different release profiles.

In a preferred embodiment, the total volume of the drug delivery portions is sufficient to contain all the drug needed for local delivery over the duration of the expansion therapy. That is, the drug delivery portions collectively house all of the anticipated doses of drug, so that drug delivery can be effected from the expander alone without the need for subsequent systemic delivery or local injection. The total drug release rate from the device is a superposition of the drug release from each of the drug delivery portions alone.

The size and shape of the tissue expander portion is selected to achieve the desired tissue expansion profile, while the size and shape of the drug delivery portion is selected to achieve the desired drug release profile. In one particular embodiment, shown in FIG. 1, the tissue expander portion is a breast tissue expander having a natural profile. A number of drug delivery portions, such as two, three, four, or five, or more drug delivery portions, are positioned about the breast tissue expander for treating pain associated with the tissue expansion process. Each of the drug delivery portions houses a drug tablet that includes lidocaine, such as about 100 mg of lidocaine, for example. The drug delivery portions are designed to release the lidocaine at a relatively continuous rate over a time window during which the patient is likely to experience pain, such as a time period in the range of about 24 hours to about 72 hours. The amount of air or space about the drug tablets in the drug delivery portion may be minimized to reduce the initial induction time of release from the device, and once release is initiated, the drug may be released at a relatively continuous rate. The drug may be driven from the device by osmotic pressure within the drug delivery portion, by diffusion, or both, until substantially all of the drug has been released into the implantation environment. The number, size, and location of the orifices can be configured to achieve the desired release rate so that substantially all of the drug is released within a selected period, such as three days. In embodiments that lack orifices, the wall through which the drug diffuses may be configured to achieve the desired release rate.

FIG. 7 illustrates plan views of various different embodiments of tissue expanders configured for local drug delivery. Each of the tissue expanders includes a breast tissue expander portion 702 and one or more drug delivery portions 704 featuring one or more orifices 766. For example, FIG. 7A illustrates a tissue expander having six smaller drug delivery portions 704A spaced about its surface. Each of the drug delivery portions 704A is circular in shape and has one or more orifices 766A. Varying the number of orifices 766A within different drug delivery portions 704A facilitates targeting varying rates of drug delivery to disparate locations.

FIG. 7B illustrates a tissue expander having one larger drug delivery portion 704B that extends about its surface. The drug delivery portion 704B is asymmetrically shaped and has a number of orifices 766B spaced about it to achieve targeted drug delivery to disparate locations.

FIG. 7C illustrates a tissue expander having two larger drug delivery portions 704C that extend about its surface. Each drug delivery portion 704C has one centrally located orifice 766C to achieve targeted drug delivery.

FIG. 7D illustrates a tissue expander having one larger drug delivery portion 704D that extends about its surface. The drug delivery portion 704D is centrally located and is circular in shape. A number of orifices 766D are spaced about the drug delivery portion 704D to achieve targeted drug delivery.

FIG. 7E illustrates a tissue expander having two drug delivery portions 704E, including a large ring shaped portion and a smaller circular portion that is positioned in the ring shaped portion. A number of orifices 766E are spaced about the larger ring shaped drug delivery portion 704E, while one orifice is positioned in the smaller circular drug delivery portion 704E.

FIG. 7F illustrates a tissue expander having a large, ring shaped drug delivery portion 704F and a number of orifices 766F spaced about the larger ring shaped drug delivery portion 704F. Of course, a range of other configurations could be employed to achieve a desired release profile to disparate locations about the implantation environment.

In one embodiment, a degradable membrane is disposed over or in one or more of the apertures to control the initiation of release of the drug from the drug delivery portion. As another example, a sheath may be positioned over a portion of some or all of the drug delivery portions to reduce the release rate, such as by reducing the osmotic surface area of the enclosure or by reducing diffusion through the enclosure wall. In still another example, the drug reservoir portion may be formed from a drug/polymer matrix or other composite designed to release at a controlled rate.

The device may be designed to administer drugs at different times. For example, the device may administer drug to achieve an immediate effect during an acute phase and to achieve a prolonged effect during a maintenance phase. The device also may administer a first dose of drug in a first period following an initial expansion session and a second dose of drug in a second period following a subsequent expansion session. To achieve such results, the device may have two drug delivery portions, one of which is configured to release a drug relatively quickly after implantation and one of which experiences an induction time before beginning release. The two drug delivery portions may have different configurations, such as different permeabilities, or the two drug delivery portions may store different forms of the drug, such as a liquid form for immediate release and a solid form to be solubilized prior to release. The two drug delivery portions may also have orifices associated with different degradable timing membranes. These embodiments can be combined and varied with other embodiments described herein to achieve the desired release profile.

In some embodiment, the drug delivery portion has multiple drug pockets or reservoirs within a single enclosure. Such a multi-reservoir device permits delivering two or more separate drugs from a single device, delivering a single drug at two different rates or at different times following implantation, or a combination thereof. For example, a first dose of the drug may be pre-programmed to release at a first time and a second dose is pre-programmed to release at a second, later time. (The term "pre-programming" here refers to designing and building the device to provide the selected release functionality.) This different pre-programming can be achieved by placing different timing membranes in different orifices associated with the different reservoirs.

II. Method of Making the Device

In another aspect, a method of making an implantable tissue expander device is provided. Generally, the method includes forming a tissue expander portion, forming an enclosure, and positioning a drug formulation in the enclosure.

The tissue expander portion is generally formed in known manners. For example, an inflatable balloon may be associated with means for inflating the balloon, such as an injection port and a filling lumen. However, the exact manner of forming the tissue expander may vary widely depending on its configuration, the intended location of implantation, and the reason for the expansion.

Forming the enclosure generally includes creating a drug formulation pocket with an enclosure wall. The enclosure wall may include a cover, a portion of the balloon, or a combination thereof. In one particular embodiment, the enclosure wall includes both a cover and a portion of the balloon. In such embodiments, the enclosure is formed by attaching the cover directly to the balloon. The cover can be attached to the outside of the balloon for ease of manufacturing, although the cover could be attached to the inside of the balloon in other embodiments. In most cases, the cover is attached to only a discrete portion of the balloon so that the cover and balloon together define a pocket or cell on the balloon surface for housing the drug formulation. However, the enclosure may be formed in other manners. For example, the enclosure may be formed by enclosing a wall to define a pocket and then separately attaching the enclosure wall to the balloon or other portions of the tissue expander. The enclosure wall can be attached to the tissue expander in any known manner, such as by using a silicone adhesive or other medical grade adhesive. As another example, the enclosure may be formed by defining a pocket or dimple for receiving a resorbable drug polymer matrix. The pocket or dimple may be pre-formed in the balloon wall or may be formed by stretching the balloon wall about the resorbable drug polymer matrix.

In embodiments, the method further includes forming a dimple or depression in at least a portion of the enclosure wall. The dimple or depression may be formed in the cover, the balloon wall, or a combination thereof. The dimple or depression may be suited for receiving the drug formulation.

In some embodiments, multiple enclosures are formed about the tissue expander device. For example, multiple enclosures may be formed by attaching multiple covers to the inflatable balloon in discrete locations. In such embodiments, the method may further include positioning the enclosures about the tissue expander device to delivery drug in a targeted manner and at a desired rate.

The method may also include forming one or more orifices through the one or more enclosures. The orifices may be formed in any portion of the enclosure, such as in the cover, the balloon wall, or both. The orifices may be formed by mechanical punching, laser ablation, laser drilling, or molding. In embodiments, the orifices may be formed simultaneously with the enclosure wall, such as by molding. The orifices may be formed either before or after the enclosure wall is attached to the tissue expanding portion and before or after the drug is loaded into the pocket. In some embodiments, multiple orifices are formed. In such embodiments, the method may further include positioning the orifices to release the drug in a targeted manner and at a desired rate.

Forming the enclosure also may comprise forming multiple different drug reservoirs or pockets in a single enclosure. In such embodiments, one or more partitioning structures may be inserted into and positioned within the pocket.

Positioning a drug formulation in the drug delivery portion generally includes positioning the drug formulation in the pocket. The loading of the drug into the pocket can be done manually or with the aid of tools and equipment. The drug formulation can be positioned in the pocket either after the enclosure is formed or while the enclosure is being formed. For example, in embodiments in which the drug formulation is in solid form the drug formulation may be positioned adjacent to the balloon wall and the cover may be placed over the drug formulation to simultaneously form the enclosure and position the drug formulation therein. Other configurations are also possible. In embodiments in which the enclosure wall includes a dimple, positioning the drug formulation in the drug delivery portion generally includes positioning the drug formulation in the dimple. In most embodiments, positioning the drug formulation in the drug delivery portion includes substantially filling the pocket with the drug formulation. Filling the pocket permits maximizing the amount of drug that can be released and reducing the induction time of initial release.

The method also may include associating one or more release controlling structures with the drug delivery portion. For example, a sheath or coating may be placed over at least a portion of the enclosure to control the rate of release of the drug. Additionally, a degradable membrane may be positioned over or in one or more of the apertures to control the initial time of release of the drug therethrough. The degradable membranes may be formed by microinjecting or inkjet printing a fluid to form a membrane at one end of the aperture, e.g., in/on the outer surface opening in the cover. For example, the fluid may be a solution comprising a resorbable material dissolved in a solvent, a suspension comprising a resorbable material in a nonsolvent, or a liquefied resorbable material. Also, the drug delivery portion may be formed from a drug/polymer composite designed to release at a controlled rate.

III. Use and Applications of the Device

The tissue expander device may be used to expand tissue and to release a drug into the tissue expansion environment. In one particular embodiment, the expansion environment is the breast area of a patient undergoing breast reconstruction, and the drug is suited for treating pain associated with the tissue expansion process. For example, the drug may a local analgesic or anesthetic, such as lidocaine, which is suited for the local treatment of pain. However, the tissue expander device also may be used to expand tissue in other locations and/or to deliver one or more other drugs for the treatment of pain or otherwise.

In one embodiment, the tissue expander device, with a self-contained drug payload, is deployed beneath the surface of the skin to expand local tissue and to simultaneously provide local, sustained delivery of at least one drug to the local tissue in an amount effective to treat the pain associated with the expansion process over at least a beginning portion of the time the tissue expander device is implanted. Following implantation of the expander, at least a portion of the payload is released from the device to nearby tissues, such as continually over an extended period in an amount effective to treat pain in the patient. In a preferred embodiment, the device resides below the skin surface, releasing the drug over a predetermined period, such as a period of hours, days, or weeks (e.g., two, three, or four weeks, a month, or more) and then the device (minus some or all of the drug) will be retrieved from the body. The device may remain implanted after the device has ceased releasing drug to continue the expansion process. The device is subsequently retrieved, and a prosthetic implant (e.g., a saline or silicone breast implant) is placed in the empty pocket or the expanded tissue is harvested for transplantation to another location.

The device may be used to deliver drugs locally to an implantation environment as an alternative to systemic delivery, which may be desirable in cases in which systemic delivery may cause undesirable side effects or result in insufficient bioavailability of the drug. The device also may be used to deliver drugs locally to an implantation environment as an alternative to local delivery via injection, which may be inconvenient.

The present intravesical drug delivery device treatment method provides extended, continuous, intermittent, or periodic release of a desired quantity of drug over a desired (predetermined) period of time. In one embodiment, the device can deliver the desired dose of drug over an extended period of time, e.g., 6 hours, 12 hours, 24 hours, 48 hours, 72 hours, 5 days, 7 days, 10 days, 14 days, or 20, 25, 30, 45, 60, or 90 days, or more. The rate of delivery and dosage of the drug can be selected depending upon the drug being delivered and the condition or disease being treated. The use of different degradation rates and/or excipient materials, along with varying the number and size of apertures in the device, can be used to tailor the device to have different release kinetics.

Figure 8:
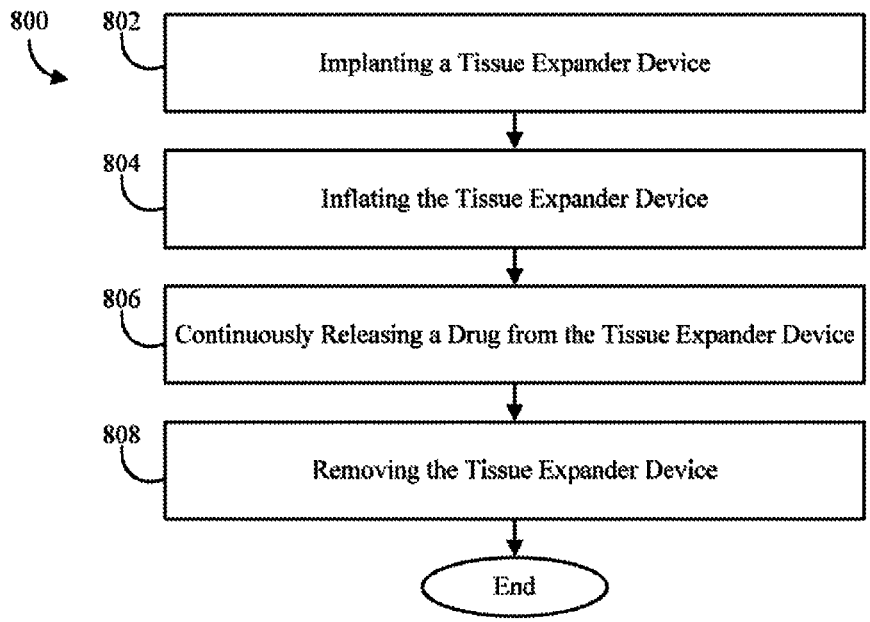
FIG. 8 is a block diagram illustrating an embodiment of a method of treating pain associated with a tissue expansion process.

In another aspect, a method of delivering drug from a tissue expander device is provided. FIG. 8 is a block diagram illustrating one embodiment of such a method. In block 802, a tissue expander device is implanted in a patient. As used herein, the term "patient" refers to human or other mammalian subjects. The tissue expander device may be an embodiment of a tissue expander described herein. The tissue expander device may be implanted using known methods and in various bodily locations. Typically, implanting the tissue expander includes implanting an inflatable balloon within the patient such that an injection port for communicating inflating material is located outside of the body and a fill lumen extends from the injection port to the inflatable balloon within the body. In some embodiments, the tissue expander device is a breast tissue expander that is implanted in the chest cavity in association with a breast reconstruction.

In block 804, the tissue expander device is inflated. For example, an inflating fluid, such as a saline solution, may be directed into an inflatable balloon implanted within the body from an injection port positioned outside of the body. The amount of inflating material that is injected through the injection port determines the degree to which the tissue expander is inflated. It should be noted that in most embodiments, the tissue expander device is not inflated in block 804 in a single expansion session. Instead, the tissue expander device is gradually or iteratively inflated over multiple expansion sessions that occur over a period of days, weeks, or months. For example, a breast tissue expander may be inflatable multiple times over a period of months to create a pocket for accepting a breast implant. For example, the balloon may be inflated incrementally, where each increment occurs at a separate session, spaced by a period of several days before the subsequent increment.

In block 806, the tissue expander device releases a drug into the implantation environment. In embodiments in which the drug is selected to relieve pain associated with inflation of the tissue expander, the tissue expander device begins releasing the drug from the device shortly after the device is implanted, and the device continues releasing the drug over a period during which the patient is likely to experience pain, such as a period in the range of about 24 hours to about 72 hours. In some embodiments, releasing the drug into the implantation environment comprises targeting the drug to treat a portion or all of the entire implantation environment, such as by releasing the drug in multiple discrete directions from multiple discrete locations on the tissue expander.

In some embodiments, the inflation of the tissue expander device in block 804 and the release of drug in block 806 may be repeated at intervals. For example, the expansion of the tissue expander device in block 804 may be followed by the release of drug in block 806 over a period to treat pain associated with the expansion process. At some point after the drug is no longer being released in block 806, the inflation may be repeated in block 804, and drug release may occur again in block 806 for a period to treat pain. Each period of drug release in block 806 may be, for example, in the range of about 24 hours to about 72 hours, but the onset of the drug release periods may be delayed or staged so that pain associated with the entire expansion process is treated.

In block 808, the tissue expander device is removed from the body. Typically, the tissue expander device is removed after a sufficient amount of skin has grown about the device. In some embodiments, the tissue expander device is removed from the body in block 808 long after the tissue expander device has stopped releasing drug in block 806. For example, the device may release drug for a period that spans several days while the device may be implanted for a period that spans several months, as the patient may only experience pain for several days even though the tissue expansion process may require several months. In other embodiments, the tissue expander device is removed from the body in block 808 shortly after the device has stop releasing drug in block 806. For example, the device may intermittently release drug over the several months that the tissue expander is implanted to treat any pain associated with the expansion sessions.

Once the tissue expander device is removed from the patient, an implant may be inserted into the empty cavity. Alternatively, the newly grown skin may be transplanted to another location in a surgical procedure. For example, the skin may be harvested to serve as a skin graft on the same or another patient.

The present disclosure may be further understood with reference to the following non-limiting example.

Example 1

Figure 9:
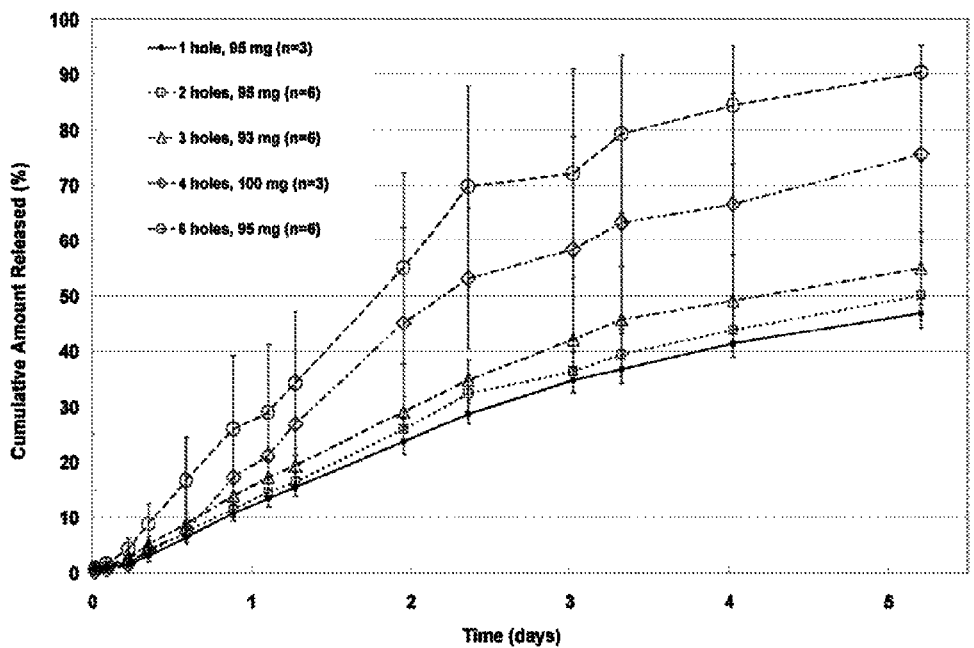
FIG. 9 is a graph illustrating the effect of orifice number on a release profile of lidocaine hydrochloride monohydrate from a silicone tube.

It was shown with tubular shaped silicone devices that lidocaine can be released from the devices in a controlled manner and that the release rate is affected by the number of orifices that are formed through a surface of the tube. FIG. 9 is a graph illustrating the effect of orifice number on the release profile of lidocaine from such a device. The orifices were about 100 micron in size. As shown, increasing the number of orifices increases the release rate.

Thus, a tissue expander that will deliver lidocaine can be configured with release orifices that will release the lidocaine into the implantation environment, and the number, size, and location of the release orifices can be configured so that most of the drug can be released within three days—the likely window during which the patient experiences pain.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A tissue expander device comprising:
   a tissue expanding portion;
   an enclosure positioned on a surface of the tissue expanding portion, the enclosure comprising:
      an enclosure wall; and
      a drug formulation pocket defined by the enclosure wall; and
   a solid drug formulation comprising a drug, the solid drug formulation housed within the drug formulation pocket.

2. The device of claim 1, wherein the tissue expanding portion comprises:
   an expandable balloon which defines a cavity for receiving an inflating fluid;
   an injection port; and
   a fill tube operable for communicating the inflating fluid from the injection port into the cavity for expanding the balloon from outside of a patient's body after the balloon has been implanted in the body.

3. The device of claim 2, wherein:
   the enclosure wall comprises:
      a portion of a wall of the expandable balloon; and
      a cover; and
   the cover is attached to the portion of the wall of the expandable balloon to define the drug formulation pocket.

4. The device of a claim 3, wherein:
   the cover is attached to an exterior surface of the wall of the expandable balloon;
   the expandable balloon is substantially impermeable to water and the drug; and
   the cover is permeable to water.

5. The device of claim 4, wherein the cover comprises one or more of the following: an aperture for releasing the drug and a material that is permeable to the drug for releasing the drug.

6. The device of claim 1, wherein at least a portion of the enclosure wall comprises a water-permeable material.

7. The device of claim 6, wherein the enclosure wall comprises an aperture that provides egress for the drug from the pocket.

8. The device of claim 1, wherein at least a portion of the enclosure wall comprises a material that is permeable to the drug.

9. The device of claim 1, wherein at least a portion of the enclosure wall comprises silicone.

10. The device of claim 1, wherein the drug formulation substantially fills the drug formulation pocket.

11. The device of claim 1, wherein the drug comprises at least one local anesthetic agent.

12. The device of claim 1, wherein the drug comprises lidocaine.

13. The device of claim 1, wherein the solid drug formulation comprises a resorbable polymer matrix.

14. A method of treating pain associated with tissue expansion in a patient, comprising:
   implanting the tissue expander device of claim 1 in the patient;
   expanding the tissue expander portion; and
   releasing an effective amount of an analgesic or anesthetic drug from the drug delivery portion for an extended period.

* * * * *